(12) United States Patent
Gen

(10) Patent No.: US 7,026,284 B2
(45) Date of Patent: *Apr. 11, 2006

(54) FORMATIVE AGENT OF PROTEIN COMPLEX

(75) Inventor: Shokyu Gen, Kyoto (JP)

(73) Assignee: BMG Incorporated, Kyoto (JP)

( * ) Notice: Subject to any disclaimer, the term of this patent is extended or adjusted under 35 U.S.C. 154(b) by 403 days.

This patent is subject to a terminal disclaimer.

(21) Appl. No.: 10/085,555

(22) Filed: Feb. 27, 2002

(65) Prior Publication Data

US 2002/0119946 A1    Aug. 29, 2002

(30) Foreign Application Priority Data

Feb. 28, 2001 (JP) .............................. 2001-107817

(51) Int. Cl.
*A61K 38/00* (2006.01)
(52) U.S. Cl. ................................. 514/2; 514/3; 514/21
(58) Field of Classification Search .................... 514/2
See application file for complete search history.

(56) References Cited

U.S. PATENT DOCUMENTS

| 4,517,175 A | * | 5/1985 | Iwabuchi et al. | ........ | 424/70.14 |
| 5,952,023 A | * | 9/1999 | Lehmberg et al. | ............ | 426/50 |

FOREIGN PATENT DOCUMENTS

| DE | 296 23 606 | 7/1999 |
| EP | 1 057 405 | 12/2000 |
| JP | 64-027471 | 1/1989 |
| JP | 02202900 | 8/1990 |
| JP | 06122631 | 5/1994 |
| JP | 8-283151 | 10/1996 |
| JP | 10-158184 | 6/1998 |
| JP | 11-075887 | 3/1999 |
| JP | 11-276162 | 10/1999 |
| JP | 2001031669 | 2/2001 |

OTHER PUBLICATIONS

Chai Salon, http://www.chaisalon.com/Recipes/recipes.htm.*
The Chemistry of Tea http://www.teatalk.com/science/chemistry.htm.*
Rita V. Copelman, Leather and Hides, http://members.aol.com/_ht_a/centralprr/fazio/page9a.htm.*
Nemours Foundation for Kids Health for Parents Milk Allergy, http://kidshealth.org/parent/medical/allergies/milk_allergy.html.*
National Cancer Institute "Prevention Agents," http://www3.cancer.gov/prevention/agents/Tea_Polyphenols.html.*
Hirofumi Tachibana, et al.; "Identification of a Methylated Tea Catechin as an Inhibitor of Degranulation in Human Basophilic KU812 Cells"; Biosci. Biotechnol. Biochem., 64 (2), 452-454, 2000.
L. Berrens, et al.; "Complement Inactivation By Allergenic Plant Pollen Extracts"; Life Sciences, vol. 60, No. 17, pp. 1497-1503, 1997.

* cited by examiner

*Primary Examiner*—Bruce H. Campell
*Assistant Examiner*—Thomas S. Heard
(74) *Attorney, Agent, or Firm*—Jordan and Hamburg LLP

(57) ABSTRACT

The present invention proposes formative agent of protein complex, in which a polyphenol is useful component, and the agent is useful as gene complex, cell adhesion inhibitor or immune tolerogen. The polyphenol of forming the agent is selected from catechin group consisting of epigallocatechin-gallate, tannic acids, or proanto-dianisidine, a protein of the protein complex is selected from proteins consisting of animal proteins composed of polypeptide chain of peptide-combined amino acids, vegetative proteins, nucleus proteins, glycogen proteins, lipo-proteins and metal proteins, the gene complex comprises by compositing genes by polyphenol catechins in order to introduce genes to cells of animals or human bodies, a cell composed of the cell adhesion inhibitor is selected from cells consisting of an animal cell including a stem cell, skin cell, mucosa cell, hepatocyte, islet cell, neural cell, cartilage cell, endothelial cell, epidermal cell, osteocyte or muscle cell isolated from human or animal organism, or sperm, ovum or fertilized egg of domestic animals or fishes and a tissue or an organ for transplantation of the immune tolerogen is selected from the tissue or the organ consisting of skin, blood vessel, cornea, kidney, heart, liver, umbilical cord, bowels, nerve, lung, placenta or pancreas.

7 Claims, No Drawings

FORMATIVE AGENT OF PROTEIN COMPLEX

BACKGROUND OF THE INVENTION

1. Field of the Invention

Present invention relates a formative agent of protein complex, in which a polyphenol is useful component, the complex is composed of cross-linking the protein molecules each other and the agent is useful as gene complex, cell adhesion inhibitor or immune tolerogen 2. Description of the Related Art A protein is treated with chemical, optical agents or heat in order to give cross-linkage and change insoluble, because the protein is generally water-soluble. Two functional cross-linking agent such as glutal-aldehyde is usually, available as chemical agent. It is well known to cross-link the protein by the enzyme activity such as trans-glutamic acid, carbonic di-imide, amber anhydride, hexsa-methylene diisocyanate (JP, H6-65280), peroxidase (JOP, H11-75887) and multi-cupper oxidase (JPO, H11-276162). However, chemical cross-linkage agents directly give cross-linkage to protein molecules and stable cross-linking structure by a covalent bond, and can not return original protein form that shows a physiological activity.

For example, diseases including an allergic reaction, an immunoreaction, cancerous spread, arteriousclerosis and other inflammatory reaction, turn out to cause cell adhesion such as between a leukocyte and blood endothelium cell, or cancerous cell and blood endothelium cell. When stimulation such viral or cell reaction irritates body organ, several inflammatory reaction happens to occur, and a leukocyte such as, neutrophil, microphage or T-cell, permeates to inflammatory parts. When an alien substance invades into living organ, an immunoreaction of self-defense means take place, and a leukocyte permeates into the organ, a leukocyte is understood to glue blood endothelium cell through the intermediation of special adhesive cell that exists on the cell surface. As adhesion molecule plays an important part in the control of an immunoreaction, it is well known to control adhesion and interaction through the intermediation of special adhesive cell. And deterrent that can control inflammatory reaction and an immunoreaction, is known (JOP H8-283151, H10-158184).

However, we can not obtain satisfactory results in the effect.

SUMMARY OF THE INVENTION

The present invention proposes formative agent of protein complex, in which a polyphenol is useful component, and the agent is useful as gene complex, cell adhesion inhibitor or immune tolerogen.

The polyphenol of forming the agent is selected from catechin group consisting of epigallocatechin-gallate, tannic acids, or proanto-dianisidine, a protein of the protein complex is selected from proteins consisting of animal proteins composed of polypeptide chain of peptide-combined amino acids, vegetative proteins, nucleus proteins, glycogen proteins, lipo-proteins and metal proteins, the gene complex comprises by compositing genes by polyphenol catechins in order to introduce genes to cells of animals or human bodies, a cell composed of the cell adhesion inhibitor is selected from cells consisting of an animal cell including a stem cell, skin cell, mucosa cell, hepatocyte, islet cell, neural cell, cartilage cell, endothelial cell, epidermal cell, osteocyte or muscle cell isolated from human or animal organism, or sperm, ovum or fertilized egg of domestic animals or fishes and a tissue or an organ for transplantation of the immune tolerogen is selected from the tissue or the organ consisting of skin, blood vessel, cornea, kidney, heart, liver, umbilical cord, bowels, nerve, lung, placenta or pancreas.

DETAILED DESCRIPTION OF THE INVENTION

Polyphenol of the present invention is defined as aromatic and aliphatic ring compounds contained phenol hydroxyl group, but no special limitation. It is preferred that the main component of catechins included in many kinds of teas (green tea, black tea and oolong tea) and the main component of tannic acids, or proanto-dianisidine included in many kinds of fruits(grape, apple, persimmon and so on), and those compounds are chiefly contained in always drunken green tea, black tea and red wine.

For example, Method how to extract green tea polyphenol from green tea is employed from dried green tea leaves by mixing in organic solvent such as water, ethanol or ethyl-acetate and main component of green tea polyphenol is catechins composed of epigallocatechin (EGCg).

Though it is easily to get polyphenol products of more than 60% purity and available for a formative agent of protein complex if the polyphenol purity is more than 60%. However, it is preferred that the purity is more than 80%. The more purity, the more effective, it is more preferred that pure EGCg, catechin or epigallocatechin are applied, when the polyphenols are applied for medical supplies.

Gene complex of the present invention is such complex in order to introduce genes to cells of human or animal organisms, and prepared by compounding the genes and catechins by polyphenol.

The cell composed of the cell adhesion inhibitor is selected from cells consisting of an animal cell including a stem cell, skin cell, mucosa cell, hepatocyte, islet cell, neural cell, cartilage cell, endothelial cell, epidermal cell, osteocyte or muscle cell isolated from human or animal organism, or sperm, ovum or fertilized egg of domestic animals or fishes.

When you use the cell, you can easily let the polyphenol stick fast to surface of cell itself or outside of cell matrix by adding the polyphenol to ordinary culture medium or storage agent applied for several kind cells, tissues and organs. Object organ and tissue for transplantation of immune tolerogen of the present invention, are organs or tissues of human or animal organism Furthermore, it is applied for medical treatment for hay fever related IgE antibody and allergic immunity treatment for an asthmatic. Said allergic immunity treatment is that the doctor gives him a hypodermic injection, starting from small amount of Allergen and gradually increasing the amount, and taking a turn for the better. It is called hyposensitization treatment and furthermore applying for hepatitis and HIV vaccine.

A protein of the protein complex in this invention is selected from proteins consisting of animal proteins composed of polypeptide chain of peptide-combined amino acids, vegetative proteins, nucleus proteins, glycogen proteins, lipo-proteins and metal proteins. It is preferred in case of applying the formative agent of protein complex that the complex is easily gotten by adding polyphenol solution to protein solution, stirring a mixture.

Sustained release preparation drugs composed of the formative agent of protein complex of the present invention, are possibly added and combined of not only polyphenol powder, but also anti-inflammatory drug, anti-allergen drug and antihistamine, furthermore, added by albumin, filler and other additives. Shapes of sustained release preparation drugs composed of the formative agent of protein complex of the present invention, include powder, a pill, an injection, paste, ointment and a suppository, dependent on the purpose, furthermore include SOD, Vitamin E; C and glutathione of anti-oxidization.

It is not known of clear cross-linking mechanism between DNA and protein by the polyphenol yet, but estimated that polyphenol shows both hydrophic and hydrophobic properties, namely soluble in both water and oil, despite polyphenol is well known as one of anti-oxidization material, but no other anti-oxidization agents show such both hydrophic and hydrophobic properties. In addition, the polyphenol shows extra good affinity to protein. Because it seems that this extra good affinity to protein comes from binding by ionic and hydrophobic combinations between phenolic hydroxyl group and protein amino group.

Immune tolerogen mechanism of polyphenol was going through the following process; treating cells, tissues and organs by polyphonol, easily binding polyphenol with said cell receptor and outside of cell matrix, preventing cell adhesion between a white blood corpuscle of a living body and a blood vessel endothelium cell of transplanted tissue, recognizing no transplanted tissue as an alien substance and looking like happening immunological rejection crisis as a result.

According to the present invention, it is easy to adjust complex, and control cell adhesion, and allergic reaction by adding the poluyphenols to proteins and DNA. The present invention provides protein cross-linking agent useful for sustained release preparation drugs, by applying the safety polyphenol for living organism, by reversibly cross-linking with cytokines, genes or enzymes in detail.

Furthermore, the present invention provides cell inhibitor useful for immune tolerogen, cancer metastasis inhibitor, anti-allergic reaction, arthritis prevention and treatment, and arteriosclerosis prevention and treatment, by treating cells, tissues and organs of human and animals with polyphenols. Furthermore, it is possible to preserve microbes long time, by adding the polyphenols to microbes. The present invention also usefully provides drug delivery pharmaceutical of cytokine, namely activated protein, by applying catechins of the polyphenol as formative agent of protein complex.

Furthermore, it is possible to reproducibly form insoluble DNA complex with several genes, introduce DNA complex to target cells and achieve good result, by applying the polyphenols as formative agent of DNA complex. Therefore, it is also possible to apply the formative agent for developing new varieties of cells in order to perform gene therapy and produce useful materials.

As catechins of the polyphenols shows good cell adhesion inhibitor, it is possible to be widely applied as immune tolerogen, anti-allergen drug, cancer metastasis inhibitor, eye drops, perfusion solution for ophthalmology, anti-inflammatory drug, and arteriosclerosis prevention and treatment. It is also possible to apply as storage preservation agent of several kinds of microbes, cord blood for transplantation, several kinds of cells, tissues and organs.

EXAMPLE

Examples and comparative examples of the present invention are explained as follows, but there is no restriction by depending on the those examples.

Example 1

Epigallocatechin-gallate (1 mg/ml) solution of 100 μl dissolved in a physiological salt solution, was added to swine insulin (crude powder, Sigma Co.) solution of 100 mg dissolved in 0.1NHCl of 10 ml, at room temperature stirring by magnetic stir. As insoluble substance was appeared after about 5 hours later, we got insulin complex from the solution by frozen dry. Eluted volume of insulin from insulin complex was estimated by glucose-oxidase method(enzyme method). Insulin was eluted 18% after 1 day later, 42% after 3 days later and 93% after 1 week later.

Comparative Example 1

Glutaric aldehyde solution was added to swine insulin (crude powder, Sigma Co.) solution of 100 mg dissolved in 0.1NHCl of 10 ml, at room temperature stirring by magnetic stir, and insulin cross-linking substance was gotten. Eluted volume of insulin from insulin cross-linking substance was estimated by similar method of example 1. However, no insulin was eluted after 1 week later.

Example 2

Epigallocatechin-gallate (1 mg/ml) solution of 100 μl dissolved in a physiological salt solution, was added to interferon α $1\times10^8$ unit dissolved in a physiological salt solution of 10 ml, at room temperature stirring by magnetic stir. As insoluble substance was appeared after about 8 hours later, we got interferon complex from the solution by frozen dry. Eluted volume of interferon from interferon complex was estimated by RIA method using Dynabot's kit. Interferon was eluted 6% after 1 day later, 32% after 3 days later and 87% after 1 week later.

Comparative Example 2

Glutaric aldehyde solution of 100 μl dissolved in a physiological salt solution, was added to interferon α $1\times10^8$ unit dissolved in a physiological salt solution of 10 ml, at room temperature stirring by magnetic stir, and insulin cross-linking substance was gotten after about 8 hours later, by frozen dry. Eluted volume of interferon from interferon cross-linking substance was estimated by similar method of example 2. However, no interferon was eluted after 1 week later.

Example 3

Epigallocatechin-gallate (1 mg/ml) solution of 50 μl dissolved in a physiological salt solution, was added to the human epithelium cell growth factor (Human EGF, frozen dry product, Ohtsuka Pharmacy) of 750 μg dissolved in 0.1 NHCl solution of 5 ml, at room temperature stirring by magnetic stir. As EGF complex substance was collected after stirring about 5 hours later by frozen dry method, Eluted volume from EGF complex was estimated by HPLC method. EGF was eluted 21% after 1 day later, 45% after 3 days later and 97% after 1 week later.

Comparative Example 3

Glutaric aldehyde solution of 50 μl, was added to the human epithelium cell growth factor (Human EGF, frozen dry product, Ohtsuka Pharmacy) of 750 μg dissolved in 0.1 NHCl solution of 5 ml, at room temperature stirring by magnetic stir. As EGF complex substance was collected after stirring about 5 hours later by frozen dry method, Eluted volume from EGF complex was estimated by similar method of example 3. However, no EGF was eluted after 1 week later.

Example 4

The rat main artery of the abdominal capvity (about 3 mm diameter) was surgically removed by about 4 cm length, and dipped 24 hours at 37° C. in DMEM culture medium added polyphenol of 1 mg/ml. The artery was surgically transplanted to rabbit carotid by blood vessel anastomosis. The transplanted rabbit was survived more than 2 months and the blood flow was observed by blood contrast. Furthermore, tissue specimen of translated blood vessel was estimated as normal specimen response still more 2 months after the transplantation.

Comparative Example 4

The rat main artery of the abdominal capvity (about 3 mm diameter) was surgically removed by about 4 cm length, and dipped 24 hours at 37° C. in DMEM culture medium. The artery was surgically transplanted to rabbit carotid by blood vessel anastomosis. The transplanted rabbit was dead 2 days after. And translated blood vessel was estimated to be fully covered by thrombus.

Example 5

Epigallocatechin-gallate (1 mg/ml) solution of 10 µl dissolved in phosphoric acid buffer solution (PBS(-)), was added to DNA solution dissolved in PBS(-) solution composed of β-galactose and a plasmid PL ZRN of 30 µM as reporter gene. DNA complex substance was collected after stirring about 5 hours later by frozen dry method. DNA appearance of DNA complex was cultured in adaptation cell stock 208F come from rat fibroblast, and introduced volume of gene is estimated as active volume of β-galactose. And converted stock volume of β-galactose gene to stable form by DNA-Epigallocatechin-gallate complex, showed extra high activity in a comparison with short-term appearance methods as a result.

Example 6

Epigallocatechin-gallate (1 mg/ml) solution of 100 µg, was added to Allergen protein of 50 mg extracted and refined from cedar pollen, and dissolved in a physiological salt solution of 10 ml, and Allergen-protein complex substance was collected after stirring about 5 hours later by frozen dry method.

Comparison of Allergen property of rat PK reaction on the complex, showed IgE repression effect.

I claim:

1. Method for forming a protein complex for a sustained release preparation drug, said method comprising treating a protein of said protein complex with a protein complex formative agent comprising a polyphenol,
    wherein said protein is selected from the group consisting of insulin, interferon α, epithelium cell growth factor (EGF), and allergen protein;
    and said polyphenol is a pure epigallocatechin gallate.

2. Method according to claim 1, wherein the weight ratio of said protein to said polyphenol is in the range of about 15–1000.

3. Method according to claim 1, comprising the steps of:
    adding said polyphenol to a solution of said protein;
    stirring said solution for about 5–8 hours;
    and drying said solution by freeze-drying.

4. A protein complex for a sustained release preparation drug comprising: a protein, and a polyphenol,
    wherein said protein is selected from the group consisting of insulin, interferon α, epithelium cell growth factor (EGF), and allergen protein;
    and said polyphenol is a pure epigallocatechin gallate.

5. The protein complex according to claim 4, further comprising at least one additive selected from the group consisting of an anti-inflammatory drug, an anti-allergen drug, an antihistamine, albumin, a filler, and an antioxidant.

6. The protein complex according to claim 4, wherein the weight ratio of said protein to said polyphenol is in the range of about 15–1000.

7. The protein complex according to claim 4, wherein said protein complex consists essentially of said protein, and said polyphenol.

* * * * *